United States Patent [19]

Resnick

[11] 4,081,467
[45] Mar. 28, 1978

[54] CATALYTIC DIMERIZATION OF HEXAFLUOROPROPYLENE EPOXIDE TO FORM PERFLUORO-2-(N-PROPOXY) PROPIONYL FLUORIDE

[75] Inventor: Paul Raphael Resnick, Wilmington, Del.

[73] Assignee: E. I. Du Pont de Nemours and Company, Wilmington, Del.

[21] Appl. No.: 697,630

[22] Filed: Jun. 18, 1976

Related U.S. Application Data

[63] Continuation-in-part of Ser. No. 564,484, Apr. 2, 1975, abandoned.

[51] Int. Cl.$^2$ ............................................. C07C 51/58
[52] U.S. Cl. .................................................. 260/544 F
[58] Field of Search ...................................... 260/544 F

[56] References Cited

U.S. PATENT DOCUMENTS

| 3,250,808 | 5/1966 | Moore et al. | 260/543 F |
| 3,940,402 | 2/1976 | Middleton | 260/293.63 |

Primary Examiner—Norman Morgenstern

[57] ABSTRACT

In the dimerization of hexafluoropropylene epoxide to form perfluoro-2-(n-propoxy)propionyl fluoride, a catalyst of a sulfonium salt is employed.

6 Claims, No Drawings

CATALYTIC DIMERIZATION OF HEXAFLUOROPROPYLENE EPOXIDE TO FORM PERFLUORO-2-(N-PROPOXY) PROPIONYL FLUORIDE

RELATED APPLICATION

The present application is a continuation-in-part of copending application Ser. No. 564,484, filed Apr. 2, 1975 now abandoned.

BACKGROUND OF THE INVENTION

The fluorocarbon ether, perfluoro-2-(n-propoxy)propionyl fluoride

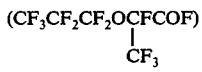

is known in the prior art and is a useful intermediate, e.g., in the preparation of perfluoro(propyl vinyl)ether. Illustrative disclosures in the prior art of the utility of these ethers are set forth in U.S. Pat. No. 3,321,532 and Du Pont Innovation, Vol. 4, No. 3, Spring 1973.

The preparation of perfluoro-2-(n-propoxy)propionyl fluoride may be through the catalytic dimerization of hexafluoropropylene epoxide. Catalysts for this reaction are disclosed in U.S. Pat. No. 3,250,808 and one catalyst system includes the use of monovalent metal fluorides, particularly alkali metal fluorides, quaternary ammonium fluorides and alkali metal perfluoroalkoxides. Other catalytic methods for carrying out the reaction disclosed in this patent involve the use of activated charcoal or high energy, particulate ionizing radiation.

SUMMARY OF THE INVENTION

The present invention is directed to the catalytic dimerization of hexafluoropropylene epoxide to form perfluoro-2-(n-propoxy)propionyl fluoride. In the dimerization of hexafluoropropylene epoxide, it is highly desirable to reduce by-products such as the trimer of hexafluoropropylene epoxide.

A catalyst of a sulfonium salt has been found to give excellent results in the formation of the hexafluoropropylene epoxide dimer. The use of a sulfonium salt has resulted in good conversions with relatively small quantities of reaction products other than the desired dimer.

An example of a suitable class of sulfonium salts is $R_1R_2R_3S^+X^-$, wherein $R_1$, $R_2$ and $R_3$ each independently of the other is an alkyl group of one to twenty carbon atoms and X, is F, $(CH_3)_3SiF_2$, Cl, Br, I, CN, NCO, NCS, $NO_2$ and $N_3$. A preferred class of sulfonium salts is of the formula

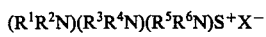

wherein the R groups individually are alkyl of up to 20 carbon atoms each alkyl having at least 2 alpha-hydrogen atoms, with the proviso that any or all of the pairs $R^1$ and $R^2$, $R^3$ and $R^4$ and $R^5$ and $R^6$ taken together with the nitrogen atom to which they are attached form a pyrrolidino or piperidino ring, any substituents being alkyl of up to 8 carbon atoms, and X is selected from the group consisting of $(CH_3)_3SiF_2$, Cl, Br, I, CN, NCO, NCS, $NO_2$ and $N_3$.

DETAILED DESCRIPTION OF THE INVENTION

The present process in formation of perfluoro-2-(n-propoxy)propionyl fluoride follows the teachings of U.S. Pat. No. 3,250,808 in the dimerization of hexafluoropropylene epoxide with the critical distinction of a different catalyst. The catalyst employed herein is a sulfonium salt. Although the starting catalytic material in the reaction procedure is a sulfonium salt, e.g., a sulfonium halide, the presence of sulfonium fluoride is considered likely to occur during the reaction, regardless of the form of the beginning catalyst. Therefore, it is understood in the present disclosure that the salt form of the catalyst may be different as the dimerization progresses.

In the catalytic dimerization of hexafluoropropylene epoxide, an undesirable result is the formation of other reaction products, particularly the trimer of hexafluoropropylene epoxide. The use of a sulfonium salt as a catalyst results in low levels of the trimer.

A preferred group of sulfonium salts is of the formula $R_1R_2R_3S^+X^-$, wherein $R_1$, $R_2$ and $R_3$ each independently of the other is an alkyl group of one to twenty carbon atoms and more preferably one to five carbon atoms, and X, is F, $(CH_3)_3SiF_2$, Cl, Br, I, CN, NCO, NCS, $NO_2$ and $N_3$. A preferred class of sulfonium salts is of the formula $(R^1R^2N)(R^3R^4N)(R^5R^6N)S^+X^-$ wherein the R groups individually are alkyl of up to 20 carbon atoms each alkyl having at least 2 alpha-hydrogen atoms, with the proviso that any or all of the pairs $R^1$ and $R^2$, $R^3$ and $R^4$ and $R^5$ and $R^6$ taken together with the nitrogen atom to which they are attached form a pyrrolidino or piperidino ring, any substituents being alkyl of up to 8 carbon atoms, and X is selected from the group consisting of $(CH_3)_3SiF_2$, Cl, Br, I, CN, NCO, NCS, $NO_2$ and $N_3$.

Sulfonium salts are well known in the prior art. Preferred sulfonium salts of the formula $(R^1R^2N)(R^3R^4N)(R^5R^6N)S^+X^-$ are disclosed in U.S. Pat. No. 3,940,402. In the present application, it is understood that the "sulfonium salt" is also inclusive of complexes. Illustratively, the salts of U.S. Pat. No. 3,940,402 can be considered as complexes.

The formation of the dimer may be undertaken in the liquid phase in the presence of an organic polar solvent of sufficient polarity to dissolve hexafluoropropylene epoxide and the intermediate ion, $CF_3CF_2CF_2O^-$. The solvent is inert to the reaction and should be a liquid at the temperature and pressure employed. Suitable solvents include aliphatic polyethers with four to sixteen carbon atoms and hydrocarbon nitriles with two to ten carbon atoms, such as the dimethyl ether of diethylene glycol, dioxane, propionitrile, benzonitrile, and acetonitrile. Other solvents which are not nitriles or polyethers include dimethyl sulfoxide, N-methyl pyrrolidone, nitroethane and tetrahydrofuran.

The general reaction conditions such as temperature and pressure are not considered critical and may be varied within wide ranges. A reaction temperature of $-80°$ C. to $200°$ C. is satisfactory with a preferred range of $-30°$ C. to $100°$ C. Additionally, the pressure in the reaction procedure is not critical to obtain the desired dimer and may range from below atmospheric pressure to several hundred atmospheres. The temperature and pressure are chosen to avoid loss of the hexafluoropropylene epoxide, e.g., by evaporation.

The concentration of sulfonium salt likewise is not critical to obtain the dimerization of hexafluoropropylene epoxide. Generally, the concentration of catalyst is at least 0.01% by weight of the hexafluoropropylene epoxide. It would be wasteful to use more than 10%.

The present process is considered to follow the direct teachings of U.S. Pat. No. 3,250,808 in the dimerization of hexafluoropropylene epoxide. The disclosure of this patent is incorporated by reference herein in relationship to the reaction conditions directed to use of a monovalent metal fluoride catalyst (e.g., catalyst concentration, solvent, temperature and pressure).

To further illustrate the present invention, the following examples are provided.

EXAMPLE 1

To a round bottom flask fitted with a magnetic stirrer, thermometer, gas inlet tube, dry ice cooled condenser and blanketed with nitrogen were added 2.1 g. $[(CH_3)_2N]_3S^+F^-\cdot SiF(CH_3)_3$, (trimethylfluorosilane complex of tris-dimethylamino sulfonium fluoride) and 50 ml. acetonitrile. An exothermic reaction took place when hexafluoropropylene epoxide was slowly bubbled into the solution. After addition of 97 g. of the epoxide at 25°–30° C., the reaction was stopped and the lower fluorocarbon layer weighing 85.4 g. was separated. Gas chromatographic analysis showed the layer to contain hexafluoropropylene epoxide dimer, trimer and tetramer. The ratio of dimer to trimer was 2.9 to 1.

EXAMPLE 2

Using the method shown in Example 1, 3.0 g. of trimethylsulfonium iodide, 50 ml. acetonitrile and 100 g. of hexafluoropropylene epoxide yielded 87.4 g. of a lower fluorocarbon layer containing hexafluoropropylene epoxide dimer, trimer and tetramer. The ratio of dimer to trimer calculated as in Example 1 was 1.4 to 1.

EXAMPLE 3

Using the method shown in Example 1, 5.0 g. of ethylmethyloctadecylsulfonium iodide, 50 ml. of diethyleneglycol dimethyl ether and 75 g. of hexafluoropropylene epoxide yielded 59.3 g. of a lower fluorocarbon layer containing hexafluoropropylene epoxide dimer, trimer and tetramer. The ratio of dimer to trimer calculated as in Example 1 was 0.66 to 1.

EXAMPLE 4

A 320 ml. stainless steel tube was charged with 1.6 g. $[(CH_3)_2N]_3S^+Cl^-$, (tris-dimethylaminosulfonium chloride), 30 ml. acetonitrile and 100 g. hexafluoropropylene epoxide. The reaction mixture was heated for 2 hours at 30° and 86 g. of a lower fluorocarbon layer was obtained. Gas chromatographic analysis showed the layer to contain hexafluoropropylene epoxide dimer, trimer and tetramer. The ratio of dimer to trimer was 3.4 to 1.

EXAMPLE 5

Using the method of Example 4, 1.5 g. of

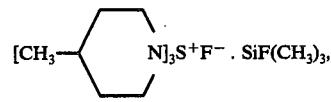

(trimethylfluorosilane complex of tris-4-methyl-piperidinosulfonium fluoride), 30 ml. acetonitrile and 100 g. of hexafluoropropylene epoxide were heated at 30° for 2 hours. Gas chromatographic analysis of the lower fluorocarbon layer which weighed 94.4 g. showed the layer to contain hexafluoropropylene epoxide dimer and trimer. The ratio of dimer to trimer was 2.1 to 1.

EXAMPLE 6

Using the method of Example 4, 1.7 g. of

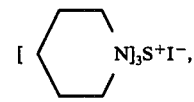

(tris-piperidinosulfonium iodide), 30 ml. acetonitrile and 100 g. of hexafluoropropylene epoxide were heated at 30° C. for 2 hours. A volatile fraction containing perfluoropropionyl fluoride was vented and the liquid products removed. The lower fluorocarbon layer which weighed 57.7 g. contained hexafluoropropylene epoxide dimer and trimer. The ratio of dimer to trimer was 12.6 to 1.

EXAMPLE 7

Using the method of Example 1, 2.0 g. of

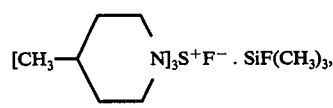

(trimethylfluorosilane complex of tris-4-methyl-piperidinosulfonium fluoride), 30 ml. of diethylene glycol dimthyl ether and 100 g. of hexafluoropropylene epoxide yielded 99.1 g. of a fluorocarbon layer containing hexafluoropropylene epoxide dimer, trimer and tetramer. The ratio of dimer to trimer to tetramer was 0.62 to 1.0 to 0.32.

EXAMPLE 8

A 320 ml. stainless steel tube was charged with 0.8 g. trimethyl sulfonium iodide, 25 ml. acetonitrile and 100 g. hexafluoropropylene epoxide. The reaction mixture was heated at 30° C for 3 hours. The lower fluorocarbon layer weighed 99 g. Gas chromatographic analysis showed the layer to consist of hexafluoropropylene epoxide dimer, trimer and tetramer. The ratio of dimer to trimer was 1.6 to 1.

COMPARATIVE EXAMPLE

A 320 ml. stainless steel tube was charged with 2.1 g. of tetraethylammonium bromide, 25 ml. acetonitrile and 100 g. hexafluoropropylene epoxide. The reaction mixture was heated at 30° C. for 3 hours. The lower fluorocarbon layer weighed 108 g. Gas chromatographic analysis showed the layer to consist of hexafluoropropylene epoxide dimer, trimer and tetramer in the ratio of 0.48 to 1 to 0.20.

What is claimed is:

1. In a process for the catalytic dimerization of hexafluoropropylene epoxide to form perfluoro-2-(n-propoxy) propionyl fluoride, the improvement comprising employing a catalyst having the formula $R_1R_2R_3S^+X_1^-$ wherein $R_1$, $R_2$ and $R_3$ each independently of the other is an alkyl group of one to twenty carbon atoms and $X_1$ is selected from the group consisting of F, $(CH_3)_3SiF_2$, Cl, Br, I, CN, NCO, NCS, $NO_2$ and $N_3$.

2. The process of claim 1 wherein said alkyl group is one to five carbon atoms.

3. The process of claim 1 wherein $X_1$ is fluorine.

4. In a process for the catalytic dimerization of hexafluoropropylene epoxide to form perfluoro-2-(n-propoxy) propionyl fluoride, the improvement comprising employing a catalyst having the formula $(R^1R^2N)(R^3R^4N)(R^5R^6N)S^+X^-$ wherein the R groups individually are alkyl of up to 20 carbon atoms, each alkyl having at least 2 alpha-hydrogen atoms, with the proviso that any or all of the pairs $R^1$ and $R^2$, $R^3$ and $R^4$, and $R^5$ and $R^6$ taken together with the nitrogen atom to which they are attached form a pyrrolidino or piperidino ring, any substituents being alkyl of up to 8 carbon atoms, and X is selected from the group consisting of $(CH_3)_3SiF_2$, Cl, Br, I, CN, NCO, NCS, $NO_2$ and $N_3$.

5. In a process for the catalytic dimerization of hexafluoropropylene epoxide to form perfluoro-2-(n-propoxy)propionyl fluoride, the improvement comprising employing a catalyst having the formula $(R^1R^2N)(R^3R^4N)(R^5R^6N)S^+X^-$ wherein the R groups individually are alkyl of up to 20 carbon atoms, each alkyl having at least 2 alpha-hydrogen atoms, and X is selected from the group consisting of $(CH_3)_3SiF_2$, Cl, Br, I, CN, NCO, NCS, $NO_2$ and $N_3$.

6. In a process for the catalytic dimerization of hexafluoropropylene epoxide to form perfluoro-2-(n-propoxy)propionyl fluoride, the improvement comprising employing a catalyst having the formula $(R^1R^2N)(R^3R^4N)(R^5R^6N)S^+X^-$ wherein each of the groups $R^1R^2N$, $R^3R^4N$ and $R^5R^6N$ is dimethylamino, and X is selected from the group consisting of $(CH_3)_3SiF_2$, Cl, Br, I, CN, NCO, NCS, $NO_2$ and $N_3$.

* * * * *